US011547279B2

(12) United States Patent
Hsia

(10) Patent No.: US 11,547,279 B2
(45) Date of Patent: Jan. 10, 2023

(54) PROXIMAL CONNECTOR ASSEMBLY FOR MEDICAL IMAGING DEVICE

(71) Applicant: Sanovas Intellectual Property, LLC, Reno, NV (US)

(72) Inventor: Alex Hsia, San Jose, CA (US)

(73) Assignee: Sanovas Intellectual Property, LLC, Reno, NV (US)

( * ) Notice: Subject to any disclaimer, the term of this patent is extended or adjusted under 35 U.S.C. 154(b) by 508 days.

(21) Appl. No.: 16/707,693

(22) Filed: Dec. 9, 2019

(65) Prior Publication Data

US 2021/0169310 A1 Jun. 10, 2021

(51) Int. Cl.
*A61B 1/00* (2006.01)
*A61B 1/06* (2006.01)
*H01R 24/58* (2011.01)
*H01R 13/17* (2006.01)
*A61B 1/05* (2006.01)
*H01R 107/00* (2006.01)

(52) U.S. Cl.
CPC ...... *A61B 1/00124* (2013.01); *A61B 1/00197* (2013.01); *A61B 1/05* (2013.01); *A61B 1/0684* (2013.01); *H01R 13/17* (2013.01); *H01R 24/58* (2013.01); *H01R 2107/00* (2013.01); *H01R 2201/12* (2013.01)

(58) Field of Classification Search
CPC ... A61B 1/00124; A61B 1/00197; A61B 1/05; A61B 1/0684; H01R 13/17; H01R 24/58; H01R 2201/12
See application file for complete search history.

(56) References Cited

U.S. PATENT DOCUMENTS

| 4,074,306 A | 2/1978 | Kakinuma et al. |
| 4,253,447 A | 3/1981 | Moore et al. |
| 8,289,381 B2 | 10/2012 | Bayer et al. |
| 8,460,182 B2 | 6/2013 | Ouyang et al. |
| 9,468,365 B2* | 10/2016 | Gunday ............. A61B 1/00154 |
| 9,927,113 B2* | 3/2018 | Birnkrant ................ H01L 33/62 |
| 10,058,235 B2 | 8/2018 | Gunday et al. |
| 2014/0275806 A1* | 9/2014 | Gunday ............... A61B 1/0684 600/249 |
| 2016/0096004 A1 | 4/2016 | Gerrans et al. |

* cited by examiner

*Primary Examiner* — Hae Moon Hyeon
(74) *Attorney, Agent, or Firm* — Blank Rome LLP

(57) ABSTRACT

A medical imaging device includes an elongated shaft having proximal and distal ends, a handle detachably connected to the shaft, and a connector assembly. The connector assembly comprises a plug at the proximal end of the shaft with an outer circumferential wall and a first plurality of electrical terminals, and a receptacle in the handle with a cavity for the plug. An image sensor is at the distal end of the shaft, and a plurality of electrical conductors electrically connected to the image sensor, are electrically connected to the first plurality of electrical terminals. An inner circumferential wall of the receptacle includes a second plurality of electrical terminals, and the outer circumferential wall of the plug has a plurality of apertures therein through which the first plurality of electrical terminals establishes an electrical connection with the second plurality of electrical terminals when the plug is inserted in the receptacle.

15 Claims, 17 Drawing Sheets

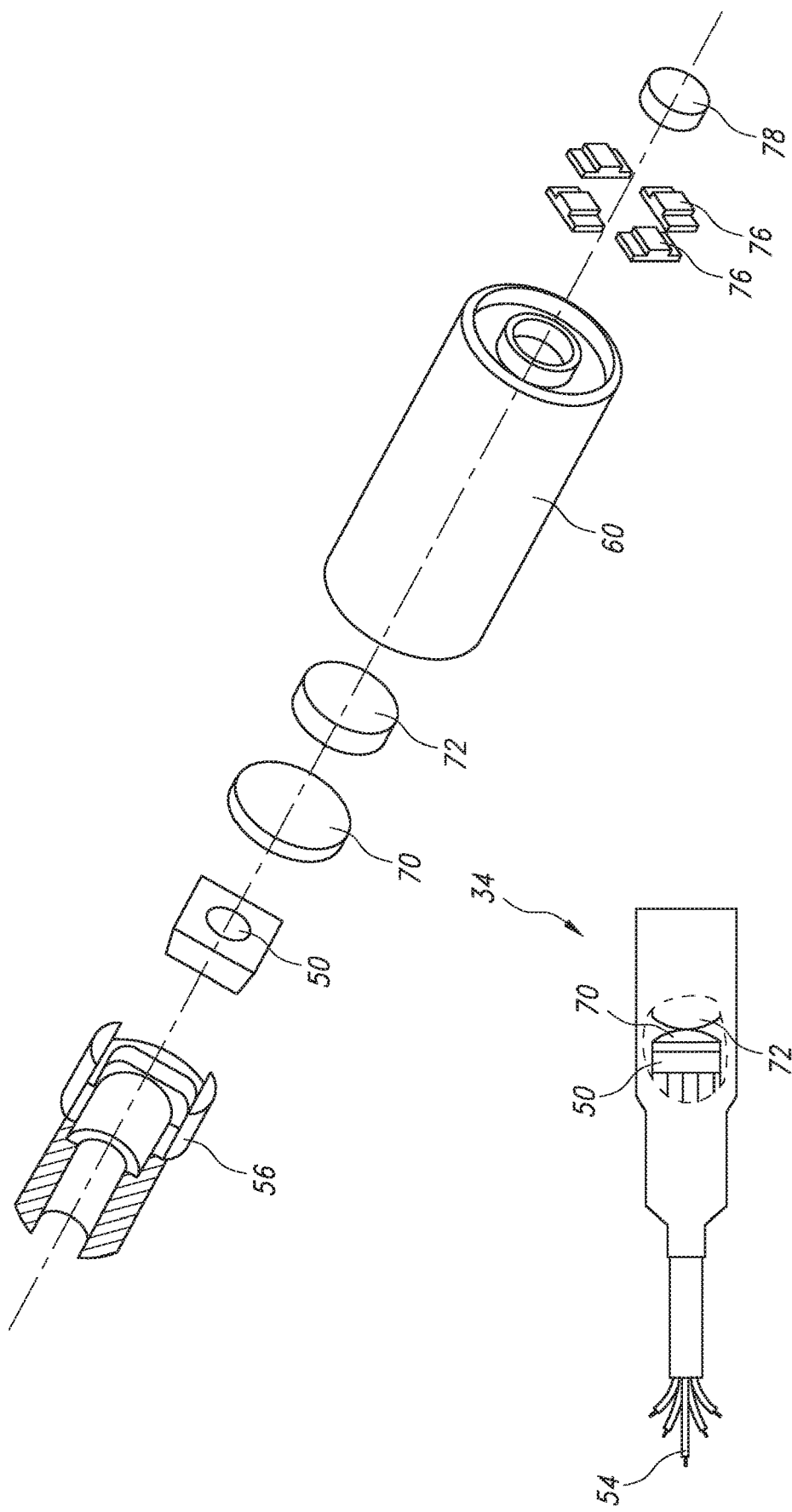

PROXIMAL CONNECTOR ASSEMBLY FOR MEDICAL IMAGING DEVICE

FIELD OF THE INVENTION

The present invention relates to medical imaging devices, such as imaging catheters and scopes. More specifically, the invention relates to such medical devices having detachable proximal ends to facilitate the removal of overlaying cannulas.

BACKGROUND OF THE INVENTION

Viewing instruments, such as a endoscopes, are generally well known in the art. Generally, an endoscope is a medical device for insertion into a body passageway or cavity that enables an operator to view and/or perform certain surgical procedures at a site inside a patient's body. The endoscope typically includes a long tubular member equipped with some type of system for transmitting images to the user, and often includes a light guide channel, channels for irrigation and suction, and a working channel for a surgical instrument. The endoscope has a proximal end that remains external to the patient, from which the operator can view the site and/or manipulate a surgical instrument, and a distal end having an endoscope tip for insertion into the body cavity of the patient.

Traditionally, these instruments have used relay optics, such as rod lenses, fiber optic bundles, or relay lenses to transmit the images from inside the body cavity of the patient to the user's eye, located at the proximal end of the endoscope, or to a camera likewise connected to the scope for subsequent display on a monitor and/or storage on an image capture device.

These traditional arrangements suffer from a number of disadvantages. First, though systems for designing, constructing, and assembling relay systems have been around for some time, these systems continue to be costly, to be time-consuming, and to demand specialized expertise. Additionally, relay systems typically employ a large number of optical components, which must be precisely fabricated and positioned in order to achieve satisfactory image quality. Finally, image degradation is inevitable with such assemblies due to the fact that the light reflecting from the viewing objects must pass through a series of optical surfaces, as back-reflection, stray light, lens surface roughness, inaccuracies in lens curvatures, and slight lens misalignments all serve to reduce image quality.

Therefore, in order to attempt to circumvent these drawbacks, endoscopes employing imaging devices at their distal end were developed. For example, U.S. Pat. No. 4,074,306 to Kakinuma et al. described the use of a solid state image pick-up device at the distal end of an endoscope. Similarly, U.S. Pat. No. 4,253,447 to Moore et al. similarly disclosed the use of a solid state imaging device such as charge coupled device (CCD) at the distal end of the scope.

With the advent and refinement of solid state image sensors lie CMOS (complementary metal-oxide semiconductor) and CCD (charge-coupled device), more expansive use of less complicated imaging catheters has also evolved. In view of the ever-increasing desire to obtain imaging devices with smaller diameters in order to view the environments within very small anatomical vessels and cavities, very thin catheters without all the channels and functionality of traditional endoscopes, but with a solid state image sensor at the distal end, have started to enjoy broader use for medical imaging.

For example, U.S. Pat. No. 8,289,381 to Bayer et al. teaches the use of an imaging catheter with a CMOS or CCD sensor at its distal tip as an auxiliary, smaller diameter imaging device within a channel of a more robust endoscope.

One shortcoming of such small diameter devices, however, is the unnecessary limitations on their use. Often, these catheters are inserted into a bodily cavity through some other, larger diameter device. This may occur, for example, when used as an auxiliary imaging device with a larger scope, as in the case of the Bayer patent discussed above, or when inserted into the body via a cannula, intubation tube, or the like. It is frequently desirable to remove the outer device, but this typically requires removing the inner imaging catheter as well. This is due to the fact that the inner imaging device is typically attached to a much wider control handle at its proximal end, which the outer shaft cannot fit over.

However, it is often desirable to leave the inner imaging device in place in the body. First, once a particular site for visualization is located, it can be difficult or time-consuming to find the site again if the imaging device is removed and then reinserted again. Additionally, it is desirable to use keep this thinner inner catheter in place while the outer cannula or other device is removed and replaced with a different cannula so that it can be used as a guidewire or "switch stick" for the new outer device.

Additionally, it also desirable to use imaging devices in which the catheter portion can be disposable without discarding the rest of the device.

For these reasons, some such devices have employed a design that renders the handle detachable. For example, U.S. Pat. No. 8,460,182 to Ouyang et al. discloses a medical instrument with a camera module at the distal tip of a cannula, which includes a CMOS, CCD, or other image sensor. The image sensor communicates with a handle connected to the proximal end of the cannula, which is detachable. In order to be detachable, the instrument has a slidable connector at its proximal end, which is plugged into a mating connector on the handle that has corresponding pin sockets for communicating with the cannula and receiving digital video signals therefrom for further transmission. As is typical, to provide this pin and socket arrangement for effectively communicating the imaging data, the slidable connector bulges radially outward, thereby resulting in a larger diameter than the rest of the cannula.

However, in order to make the imaging catheter detachable from the handle, a connector suitable for communication the imaging data from the distal image sensor must be employed. As shown in FIGS. 1A-B, this is typically in the form of a Fischer® or other pinned connecter (20), which plug into a corresponding socket (24) on the handle (26). This has several disadvantages.

First, when dealing with small diameter catheters, this connector (20) results in a bulge at the proximal end of the catheter. While smaller than the even wider handle, it still results in a larger diameter on the catheters proximal end than the rest of the catheter. Very small diameter catheters are employed for the purpose of navigating very small environments, and thus, any outer cannula used with it will likewise have a very small diameter. Yet, in order to be able to remove the outer cannula, the inner diameter of the outer cannula can only be so small, as it needs to be large enough to accommodate the connector (20) as it slides over it.

Additionally, the amount of data that can be transmitted is limited to the pins (22) that are spaced apart in the cross-sectional area of the connector (20). This, of course, is limited by the diameter of the connector (20), which cannot be too large.

What is desired, therefor, is an imaging device with a distal imager that can remain in the body when an outer cannula or other device is removed over it. What is further desired is a small diameter imaging device that can maintain the small diameter at its proximal end so that small diameter outer cannulas can be used. What is also desired is a small diameter imaging device that can communicate large amounts of data from its distal end to its handle. What is also desired is an imaging device in which the catheter portion is disposable.

SUMMARY OF THE INVENTION

Accordingly, it is an object of the present invention to provide an imaging device with an image sensor at its distal end and a proximal end with a detachable connection to its handle.

It is also an object of the present invention to provide such a detachable imaging device that does not employ traditional pin connectors.

It is a further object of the present invention to provide such a detachable imaging device that maximizes the amount of data from the distal sensor that can be communicated through its connection to the handle.

In order to overcome the deficiencies of the prior art and to achieve at least some of the objects and advantages listed, the invention comprises a medical imaging device, including an elongated shaft having a proximal end and a distal end, a handle detachably connected to the elongated shaft, and a connector assembly by which the elongated shaft is detachably connected to the handle. The connector assembly comprises a plug at the proximal end of the shaft, the plug having an outer circumferential wall, wherein the plug includes a first plurality of electrical terminals, and a receptacle in the handle, the receptacle having an inner circumferential wall defining a cavity that accommodates the plug. The imaging device includes an image sensor at the distal end of the elongated shaft, and a plurality of electrical conductors electrically connected to the image sensor, extending through the elongated shaft, and electrically connected to the first plurality of electrical terminals in the plug, wherein the inner circumferential wall of the receptacle includes a second plurality of electrical terminals, and wherein the outer circumferential wall of the plug has a plurality of apertures therein through which the first plurality of electrical terminals establish an electrical connection with the second plurality of electrical terminals when the plug is inserted in the receptacle.

In certain advantageous embodiments, the plug has a longitudinal axis, and the second plurality of electrical terminals comprise a plurality of pins extending radially from the inner circumferential wall of the receptacle toward the longitudinal axis of the plug when the plug is inserted in the receptacle.

In some cases, the first plurality of electrical terminals comprise a first plurality of pins extending radially from the longitudinal axis of the plug toward the outer circumferential wall, and the second plurality of electrical terminals comprise a second plurality of pins extending radially from the inner circumferential wall of the receptacle toward the longitudinal axis of the plug when the plug is inserted in the receptacle, such that the first plurality of pins contact the second plurality of pins when the plug is inserted in the receptacle.

In some of these embodiments, the second plurality of pins are spring-loaded such that the second plurality of pins descend from an unlocked position into a locked position when first plurality of pins become aligned with the second plurality of pins as the plug in inserted into the receptacle. In some cases, the receptacle further comprises a cam that, when moved from a first position to a second position, moves the second plurality of pins from the locked position to the unlocked position to release the plug.

In some embodiments, at least some of the first plurality of electrical terminals are longitudinally offset from at least some others of the first plurality of electrical terminals. In some of these embodiments, at least some of the first plurality of electrical terminals are circumferentially offset from at least some others of the first plurality of electrical terminals.

In certain embodiments, the elongated shaft has an outer diameter of about 4 mm or less. In some cases, the outer diameter is 3.8 mm, and in some cases, the outer diameter is 3.6 mm.

In certain advantageous embodiments, the image sensor comprises a CMOS sensor. In other embodiments, the image sensor comprises a CCD sensor.

In some embodiments, the imaging device further includes at least one lens positioned distally of the image sensor. In some of these embodiments, the at least one lens comprises two plano-convex lenses positioned distally of the image sensor.

In certain embodiments, the imaging device further includes at least one illumination device in the distal end of the elongated shaft. In some of these embodiments, the at least one illumination device comprises a plurality of LEDs (light-emitting diodes) arranged circumferentially in the distal end of the elongated shaft.

The invention also comprises a medical imaging device, including an elongated shaft having a maximum outer diameter, a proximal end and a distal end, a handle detachably connected to the elongated shaft, and a connector assembly by which the elongated shaft is detachably connected to the handle. The connector assembly includes a plug at the proximal end of the shaft, the plug having an outer circumferential wall, wherein the plug includes a first plurality of electrical terminals, and a receptacle in the handle that accommodates the plug. The imaging device includes an image sensor at the distal end of the elongated shaft, and a plurality of electrical conductors electrically connected to the image sensor, extending through the elongated shaft, and electrically connected to the first plurality of electrical terminals in the plug, wherein the receptacle includes a second plurality of electrical terminals, wherein the outer circumferential wall of the plug has a maximum diameter that is not greater than the maximum outer diameter of the elongated shaft, and wherein the first plurality of electrical terminals establish an electrical connection with the second plurality of electrical terminals when the plug is inserted in the receptacle.

BRIEF DESCRIPTION OF THE DRAWINGS

FIG. 3A is a partially exposed, side view of the distal end of the imaging device of FIG. 2.

FIG. 3B is an isometric view of a camera head of the imaging device of FIG. 2.

DETAILED DESCRIPTION OF THE INVENTION

The following detailed description illustrates the technology by way of example, not by way of limitation, of the principles of the invention. This description will enable one skilled in the art to make and use the technology, and describes several embodiments, adaptations, variations, alternatives and uses of the invention, including what is presently believed to be the best mode of carrying out the invention. One skilled in the art will recognize alternative variations and arrangements, and the present technology is not limited to those embodiments described hereafter.

Figure 1A:
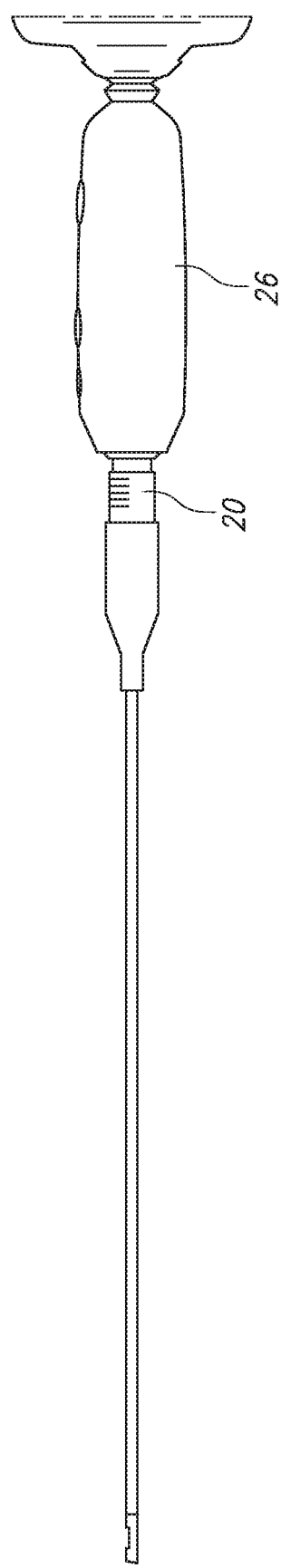
FIG. 1A is a side view of prior art imaging devices.
Figure 1C:
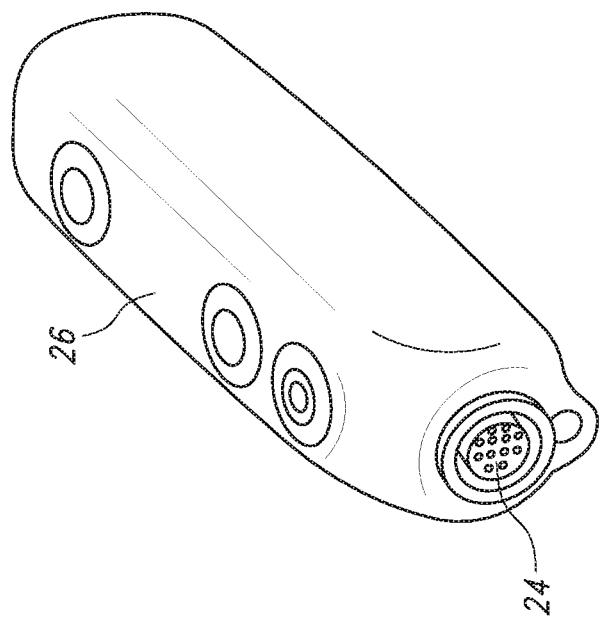
FIGS. 1B-C are isometric views of prior art connectors used with imaging devices.
Figure 1B:
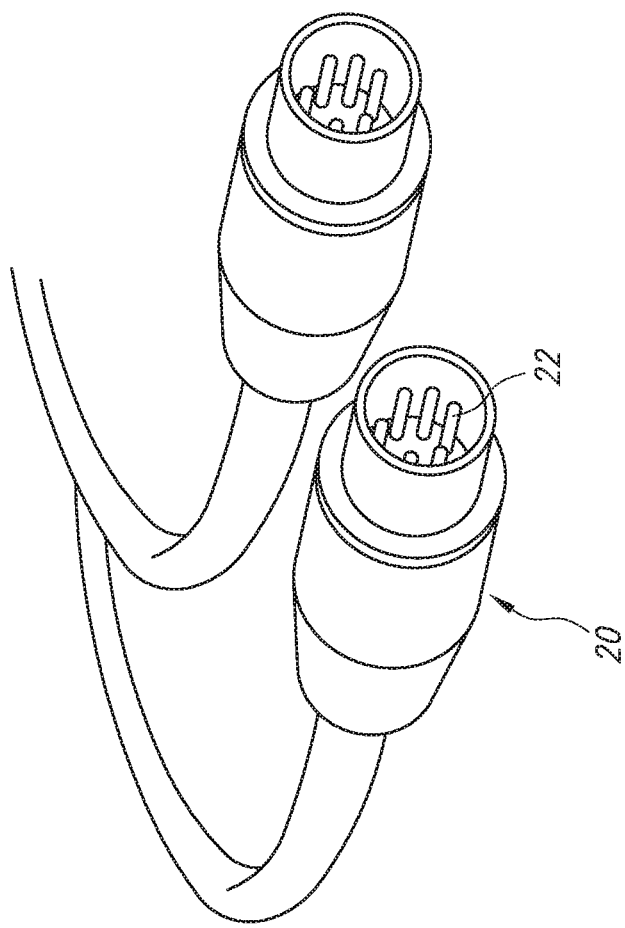
Figure 2:
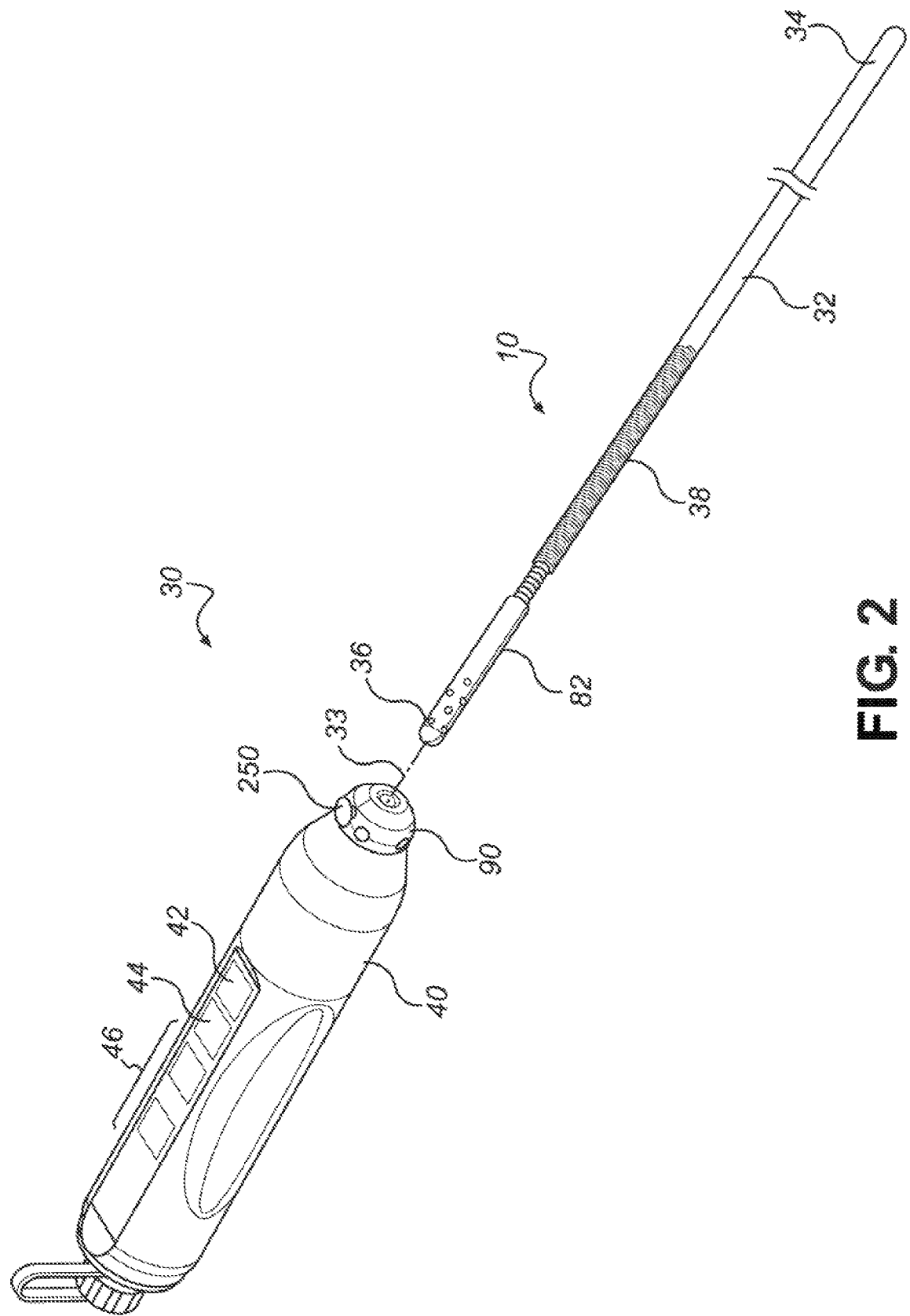
FIG. 2 is an isometric view of a system according to the invention.

FIG. 2 illustrates one exemplary embodiment of a medical imaging device (30) in accordance with the invention. An imaging catheter includes an elongated shaft (32) having a generally cylindrical body and an inner lumen. The elongated shaft (32) has a distal end (34) for insertion into the body of a patient via an incision or natural orifice, in which the optical components of the device are housed, as further described below. The shaft (32) also has a proximal end (36) connected to a handle (40), which provides several functions. First, the handle (40) is used to hold the catheter and manipulate it in whatever bodily cavity or vessel it is inserted into. The handle (40) also typically includes basic controls associated with viewing and recording the anatomical environment, such as image capture (42), recording video (44), and adjusting the brightness (46). The handle (40) may include other controls as well, such as, for example, deflection control of the distal tip of shaft (32).

The elongated shaft (32) has a longitudinal axis (33), along which the length of the catheter is defined. The elongated shaft (32) may be constructed from any suitable rigid or semi-rigid material, such as, for example, polyether amide (PEBA), Pebax® or polyurethane. The diameter of the catheter should usually be made as small as possible.

Typically, the outer diameter of the shaft (32) is less than about 6 mm. Preferably, the outer diameter of the catheter body is less than 4 mm (e.g., 3.6 mm, 3.8 mm). In certain advantageous embodiments of the invention, the inner lumen has a diameter of at least about 1.2 mm.

An inner portion of the shaft (32) of the catheter device (10) has an inner support element (38), such as a coil, to assist the bending motion of the elongated body. The shaft (32) can be molded over during the catheter extrusion process, or the catheter body may be molded or extruded in a first step and the element (38) subsequently disposed within its inner lumen. This may comprise, for example, a coil, such as that described in U.S. Pat. No. 10,058,235 to Gunday et al. (the disclosure of which is incorporated by reference herein in its entirety), or a braided sheath, such as that disclosed in U.S. Published Application No. US 2016/0096004 by Gerrans et al. (the disclosure of which is incorporated by reference herein in its entirety). This prevents the elongated shaft (32) from kinking and provides improved torque, allowing the distal end (34) of the catheter to be stiffer while the catheter is being pushed through the bodily vessel.

In some embodiments, the shaft (32) includes at least two channels that accommodate pull wires for deflecting the distal end (34) in order to steer the catheter or adjust the angle of view at a target site. In some embodiments, the distal tip is a separate member attached to the main body of the shaft, and is fashioned from a suitable material that has a more desirable flexibility, such as, for example, a polymer plastic like polyether ether ketone (PEEK), as disclosed in U.S. Published Application No. 2016/0096004 by Gerrans et al.

In certain advantageous embodiments, the elongated shaft (32) includes imaging markers, such as radiopaque rings, located throughout the length of, or at or near, the distal end (34). Such markers can be selected and appropriately positioned in order to reflect the relevant waves of various imaging modalities (e.g., x-ray) in order to allow the use of such modalities to assist with the precise positioning of the catheter. In another advantageous embodiment, a braided sheath (discussed further below) is radiopaque.

As illustrated in FIG. 3A, the distal end (34) of the elongated shaft (32) includes a solid state image sensor (50). In some cases, this is a CMOS (complementary metal-oxide semiconductor) sensor, and in others, this is CCD (charge-coupled device) sensor. Alternatively, a QIS (quanta image sensor) may be employed.

The image sensor (50) has a sufficiently small outer diameter, typically about 1 mm-2 mm. in some embodiments, the sensor diameter is about 0.5 mm.

A plurality of electrical conductors (54) are electrically connected to the image sensor (50), and extend down through the elongated shaft to transmit the digital signals toward the proximal end, and are electrically connected to the first plurality of electrical terminals in a plug, further described below.

Figure 3C:
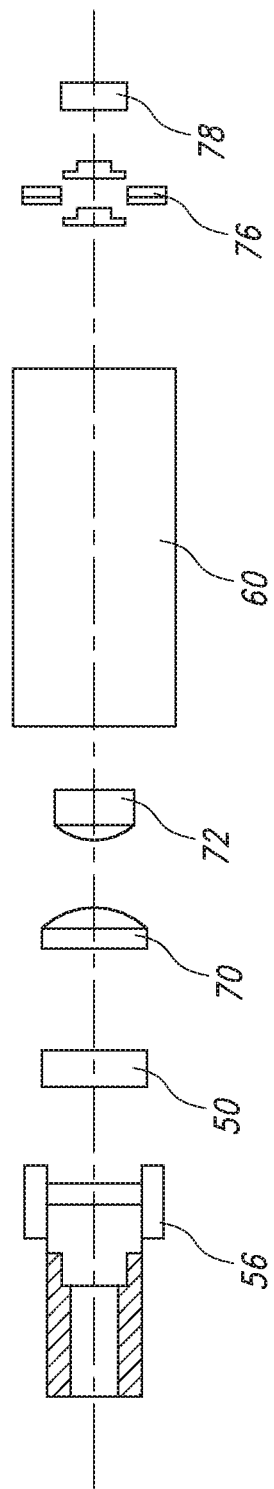
FIG. 3C is a side view of a camera head of the imaging device of FIG. 2

Referring to FIGS. 3B-C, one advantageous embodiment of the optical components is shown. In this embodiment, a separate housing (60) connected to the distal end (34) of the shaft (32) houses various components. The housing (60) is made with any suitable material, such as plastic or metal, and has any desired shape. One or more lenses (70, 72) are positioned in the housing (60), which in the example shown, includes two positive lenses, plano-convex lenses (70) and (72), positioned opposite of each other such that the convex sides of the lenses are facing each other. It is understood that any other lens type and arrangement may be used in accordance with the present invention, as desired.

The image sensor (50) is positioned proximally of the lenses (70, 72) and coupled to a sensor mount (56) to position the sensor (50) in the housing (60). The housing (60) also houses one or more illumination devices (76), such as LEDs, positioned distally of the lenses (70, 72). It is understood that other types of illumination devices may be used.

The distal end of the housing (60) also includes a cover glass (78), which seals the distal end of the housing (60) to protect the imaging and optical components therein.

The image sensor (50) and/or lenses (70, 72) may be oriented substantially parallel to the longitudinal axis (33) of the elongated shaft (32), or may be positioned at a certain angle relative to the longitudinal axis (33) in order to allow for better imaging of particular anatomies. In some embodiments, the image sensor (50) and/or lenses (70, 72) may be tilted to different angles by a tilting mechanism while being operated, depending on the desired angle of view, or may be advanced distally or proximally to better focus the image.

Figure 4A:
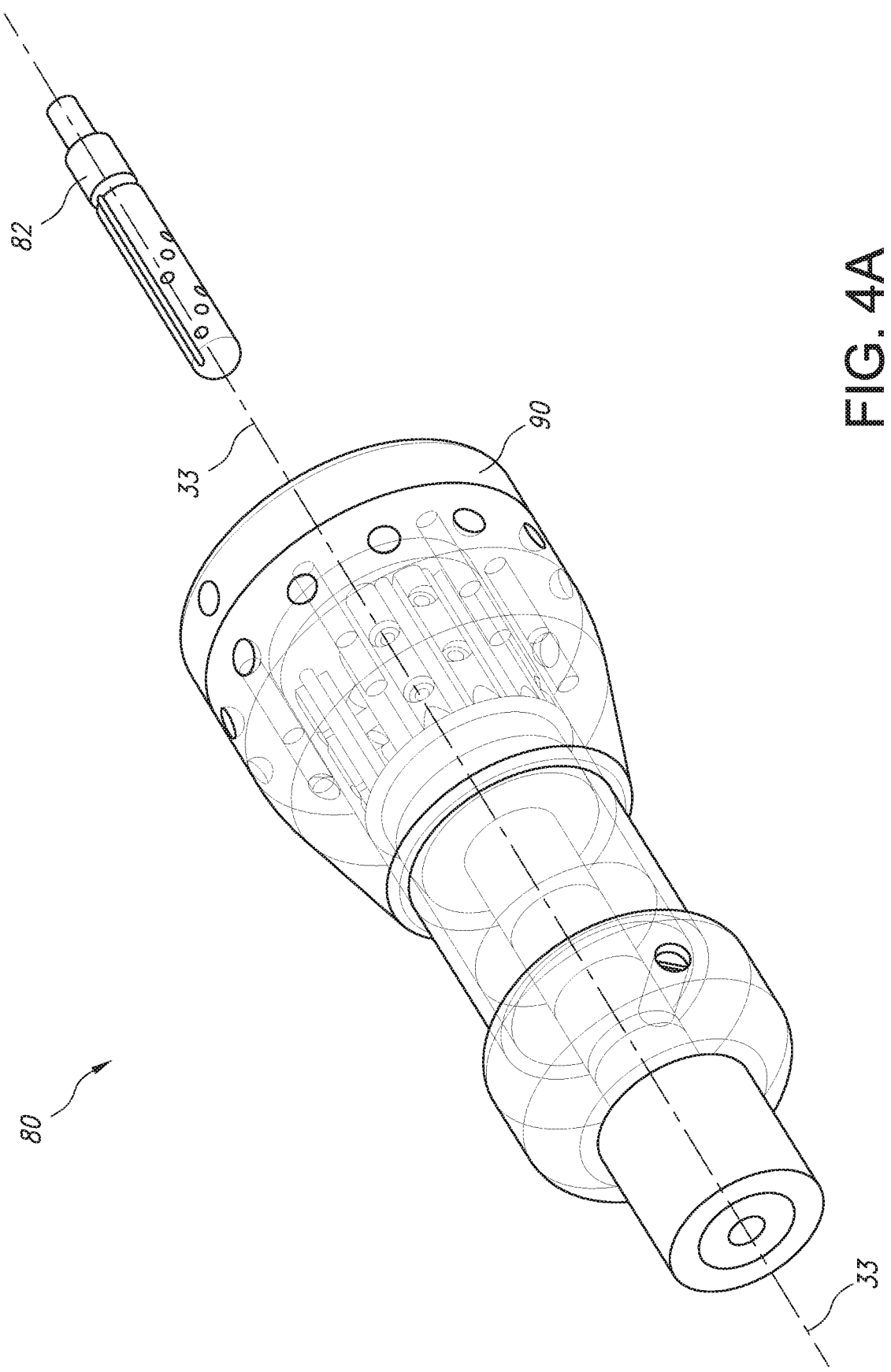
FIG. 4A is an exposed, isometric view of a connector assembly used with the imaging device of FIG. 2.

Referring to FIG. 4A, one embodiment of a connector assembly (80) by which the elongated shaft (32) is detachably connected to the handle (40) is shown. The connector assembly (80) includes a male portion in the form of a plug (82) at the proximal end (36) of the elongated shaft (32), as well as a female portion in the form of a receptacle (90).

Figure 4B:
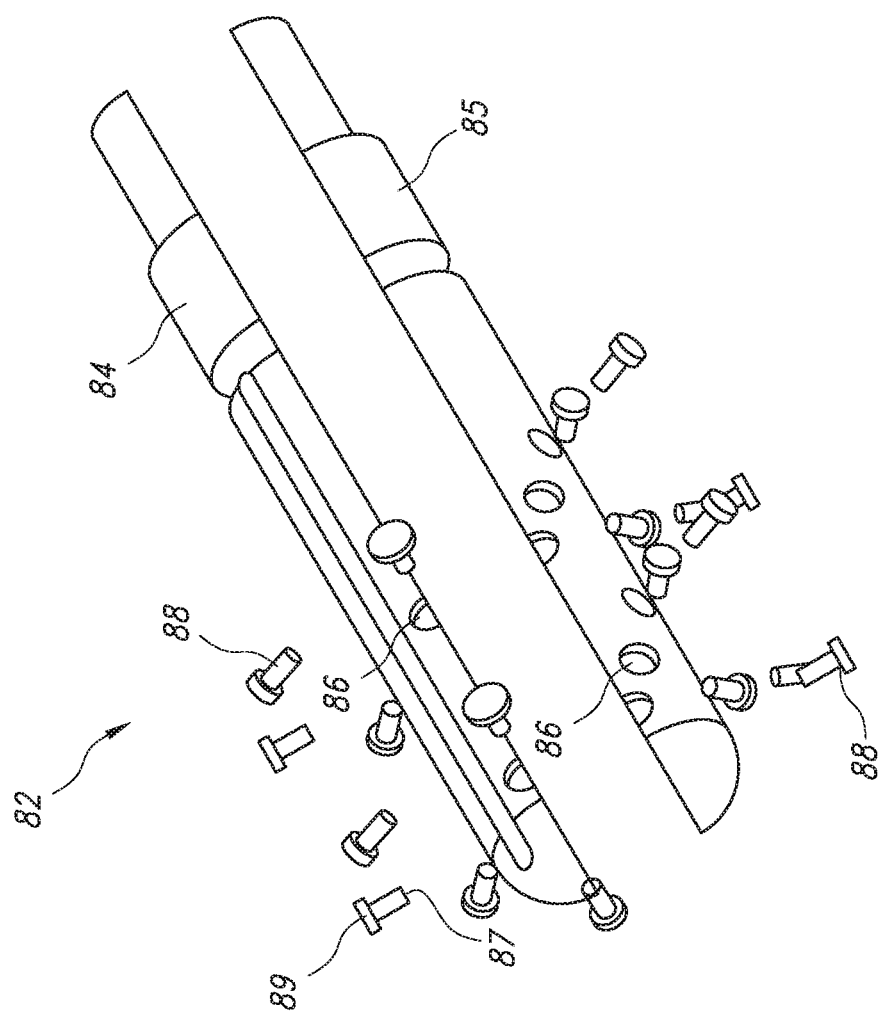
FIG. 4B is an exploded, isometric view of the plug of the connector assembly of FIG. 4A.

As shown in FIG. 4B, the plug (82) is formed of first and second halves (84, 85) that are joined together and have a plurality of apertures (86) passing through the walls thereof. The apertures (86) accommodate a plurality of metallic pins (88) disposed therein. Each of the pins (88) has a tip (87) that is electrically connected (via soldering or other method) to the conductors (54) extending through the elongated shaft (32), such that the electrical signals from the image sensor (50) are communicated thereto. The pins (88) extend radially from the longitudinal axis (33) of the plug (82) toward its outer circumferential wall. The pins (88) have an enlarged head (89) that serves as an electrical terminal by virtue of the aperture (86).

In advantageous embodiments, the pins (88) are arranged in a pattern to maximize the number of electrical terminals provided. The pins (88) are longitudinally offset from each other to take advantage of the length of the shaft (32), and the length of the plug (82) can be modified in order to increase the number of pins that can be used. Similarly, the pins (88) can be circumferentially offset from each other in order to take advantage of the circumference of the plug (82) to increase the number of pins. In the embodiment shown, the pins (88) are both longitudinally and circumferentially offset in order to maximize the number of pins that can be employed. With this arrangement, a large amount of data can be transmitted to the outer circumferential surface of the plug (82).

Figure 4C:
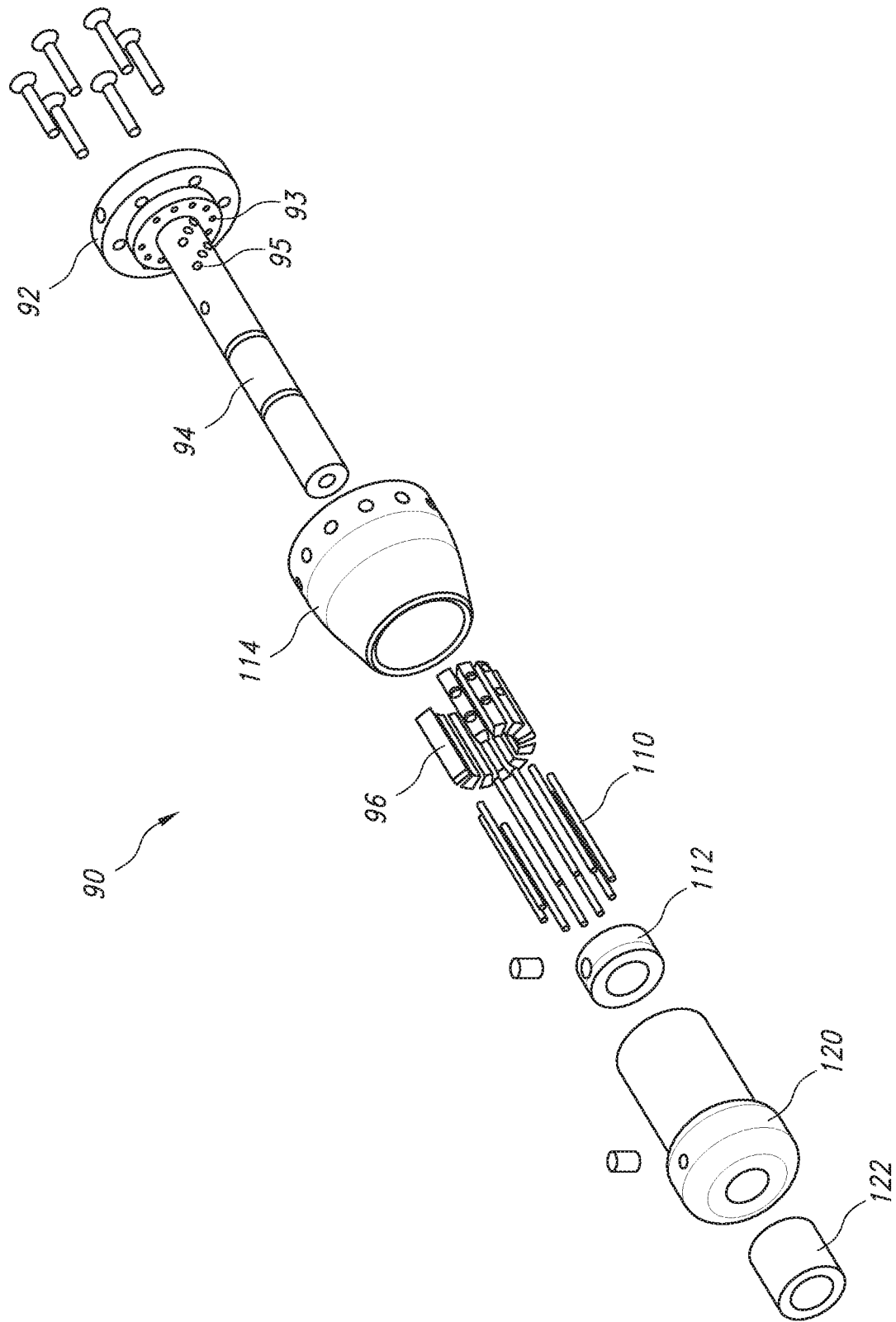
FIG. 4C is an exploded, isometric view of the receptacle of the connector assembly of FIG. 4A.
Figure 4D:
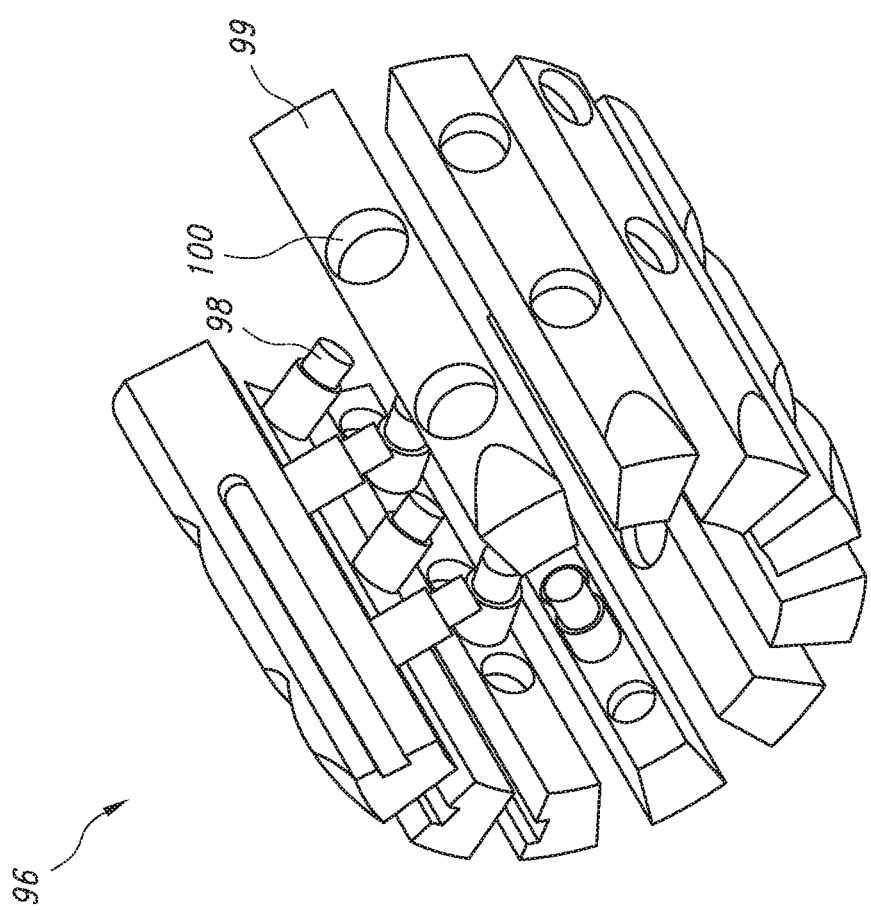
FIG. 4D is an isometric view of the pin assembly of the receptacle of FIG. 4C.

Referring to FIGS. 4C-D, the receptacle (90) includes a base (92) having a shaft portion (94) that extends through the length of the receptacle (90) when assembled. A pin assembly (96) containing a second plurality of pins (98) is disposed over the shaft portion (94), which has a plurality of apertures (95) through which the pins (98) will extend into the inner lumen of the shaft portion (94). A plurality of guide pins (110) are inserted into a plurality of corresponding apertures (93) of the base (92) in order to center the pin assembly (96), and a collar (112) and outer cover (114) secure it in place. A cam lock (120) and stop cover (122) are disposed over the proximal end of the shaft portion (94).

As shown in FIG. 4D, the pin assembly (96) includes a plurality of pins (98) retained on a plurality of pin support members (99) and extending through a plurality of apertures (100) therein. Like the pins (88) of the plug (82), these pins (98) are arranged longitudinally and circumferentially offset in a pattern corresponding to that of the pins (88). The pins (98) have enlarged heads that retain them in the pin assembly (96), and pointed ends extending radially from the inner circumferential wall toward the center of the pin assembly (96).

Figure 4E:
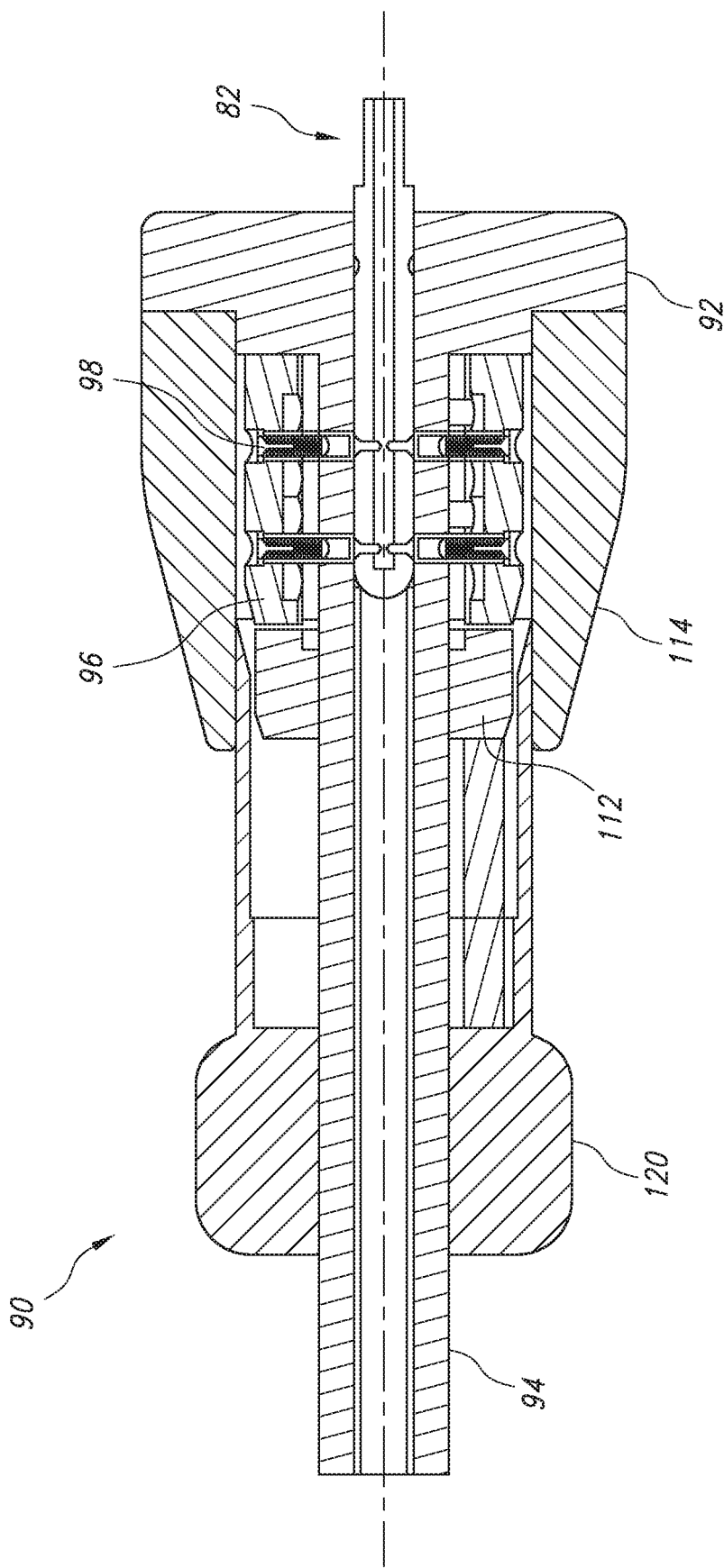
FIG. 4E is a cross-sectional view of the connector assembly of FIG. 4A when in a connected position.

As shown in FIG. 4E, the connector assembly (80) connects the proximal end of the elongated shaft (32) to the handle (40) by plugging the plug (82) into the receptacle (90). The pins (98) are spring loaded, such that, when aligned with pins (88) of the plug (82), the pins (98) descend into the apertures (86) of the plug (82) to click into place, thereby establishing an electrical connection between the pins (88) and the pins (98). As a result, a large amount of data from the image sensor (50) is communicated to the pins (98), which are themselves electrically connected to a processor in the handle (40) or some other device.

While the connecting pins (88, 98) described above have been described as all metal pins, this is not required. For example, in some embodiments, the metallic pins comprise a metal wire within an outer polymer. Other materials may be employed, as long as it is sufficient to conduct the electrical signals.

It should also be noted that, while the plug (82) is generally concentric with the elongated shaft, the outer surface of the plug (82) need not be cylindrical, and may have recesses, protuberances, undulations, and the like. Additionally, while the connector assembly (80) may be employed with an imaging catheter, it may also be employed with other narrow imaging devices, such an optical stylet, endoscope, or the like. Accordingly, the handle (40) may be a fairly sophisticated control device like that described above for use with the imaging catheter, or may simply be an outer housing of the connector assembly (80) adapted to be connected to a control box or other device.

Figure 5A:
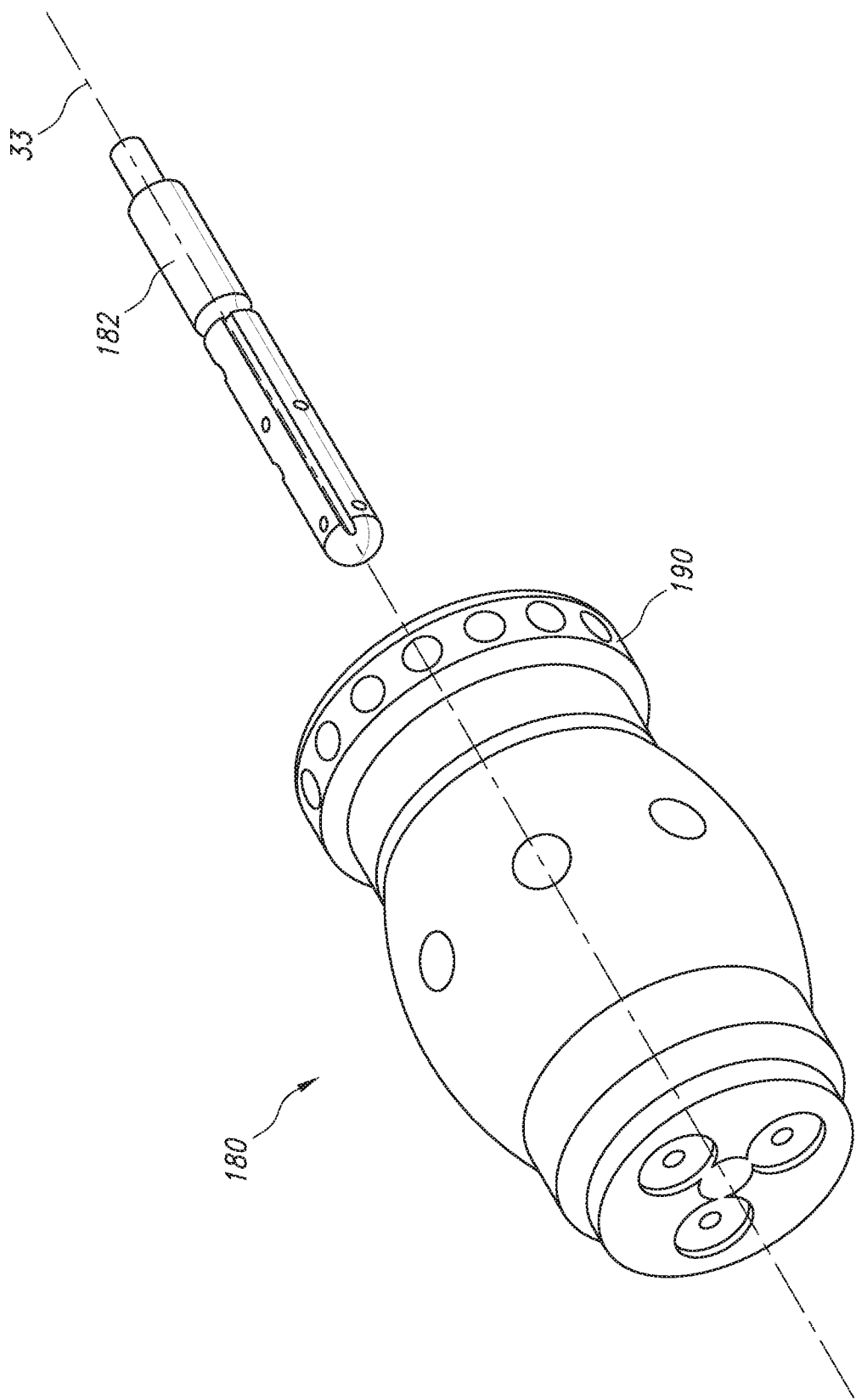
FIG. 5A is an isometric view of a connector assembly used with the imaging device of FIG. 2.

Referring to FIGS. 5A-E, another embodiment of a connector assembly (180) is shown. As shown in FIG. 5A, the connector assembly (180) includes a male plug (182) at the proximal end (36) of the elongated shaft (32), as well as a female receptacle (190).

Figure 5B:
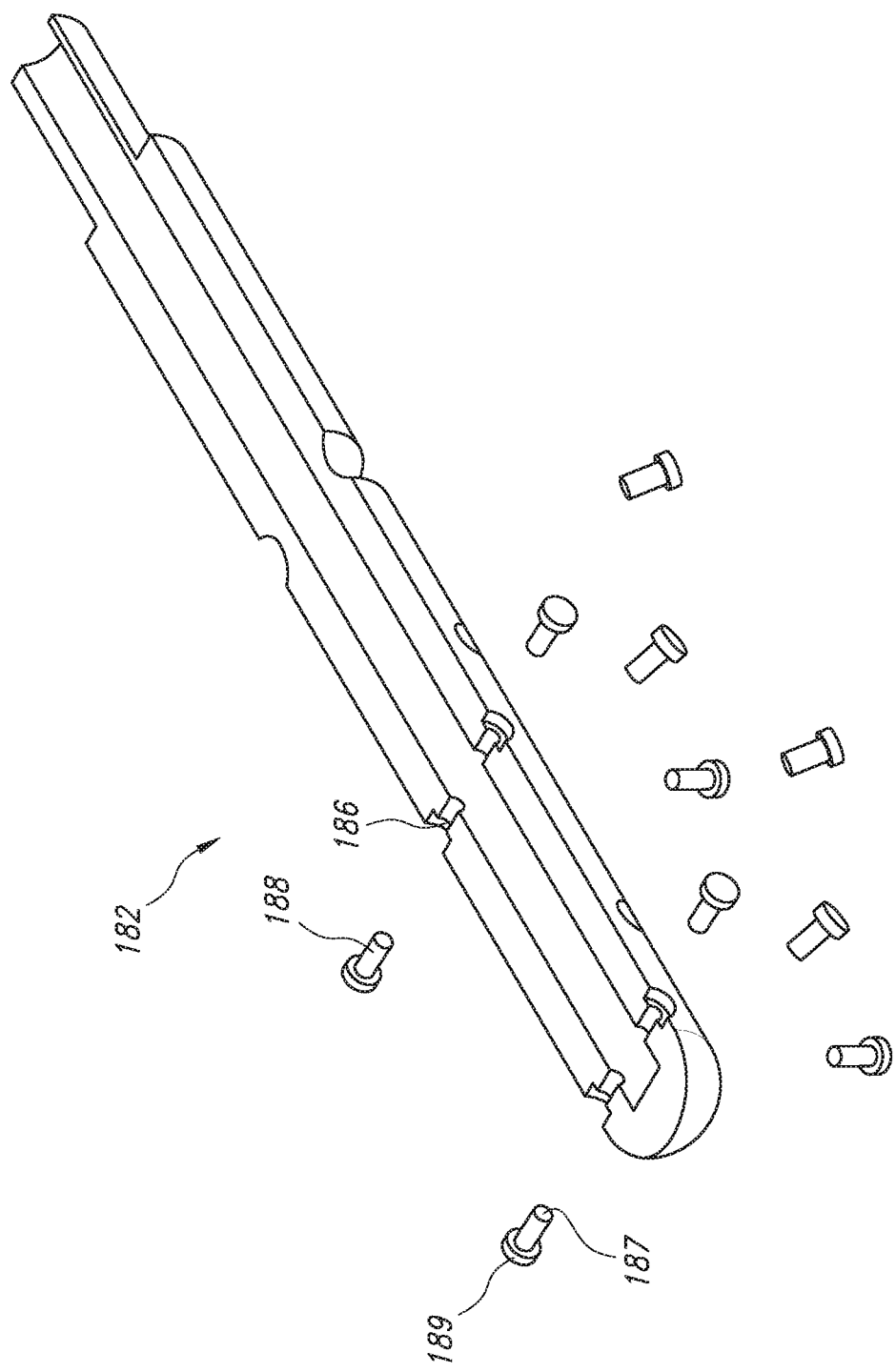
FIG. 5B is an exploded, isometric view the plug of the connector assembly of FIG. 5A.

Referring to FIG. 5B, the plug (182) similarly has a plurality of apertures (186) passing through the wall of the plug (182), which accommodate a plurality of metallic pins (188) disposed therein. Each of the pins (188) has a tip (187) that is electrically connected to the conductors (54) extending through the elongated shaft (32), such that the electrical signals from the image sensor (50) are communicated thereto. The pins (188) extend radially from the longitudinal axis (33) of the plug (182) toward its outer circumferential wall, and in this case, are arranged in sequences parallel to the longitudinal axis (33), as opposed to the more curved sequences of the previous embodiment. The pins (188) have an enlarged head (189) that serves as an electrical terminal by virtue of the aperture (186). As in the previous embodiment, the pins (188) are arranged in a pattern to maximize the number of electrical terminals provided, longitudinally and circumferentially offset from each other.

Figure 5C:
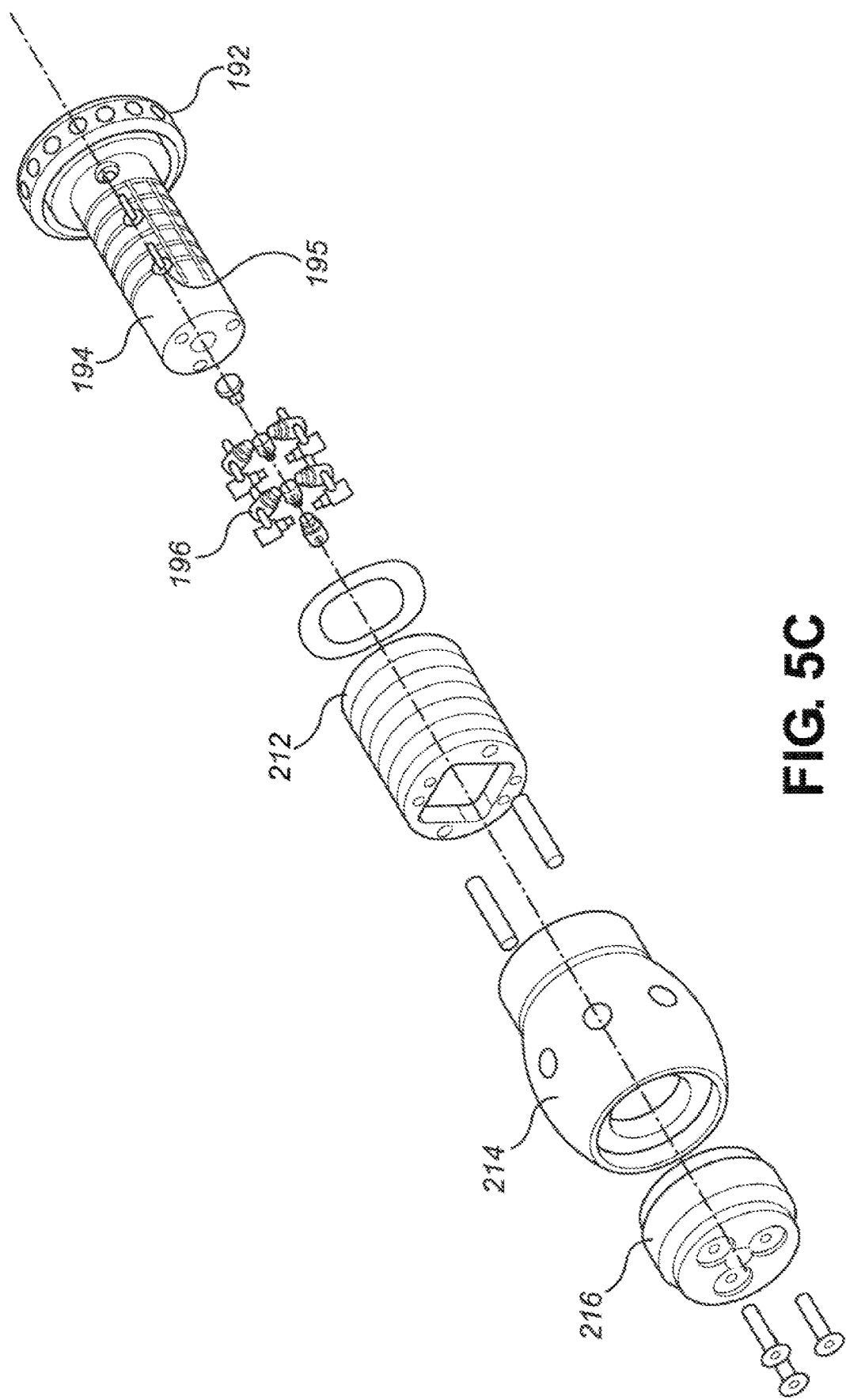
FIG. 5C is an exploded, isometric view of part of the receptacle of the connector assembly of FIG. 5A.
Figure 5D:
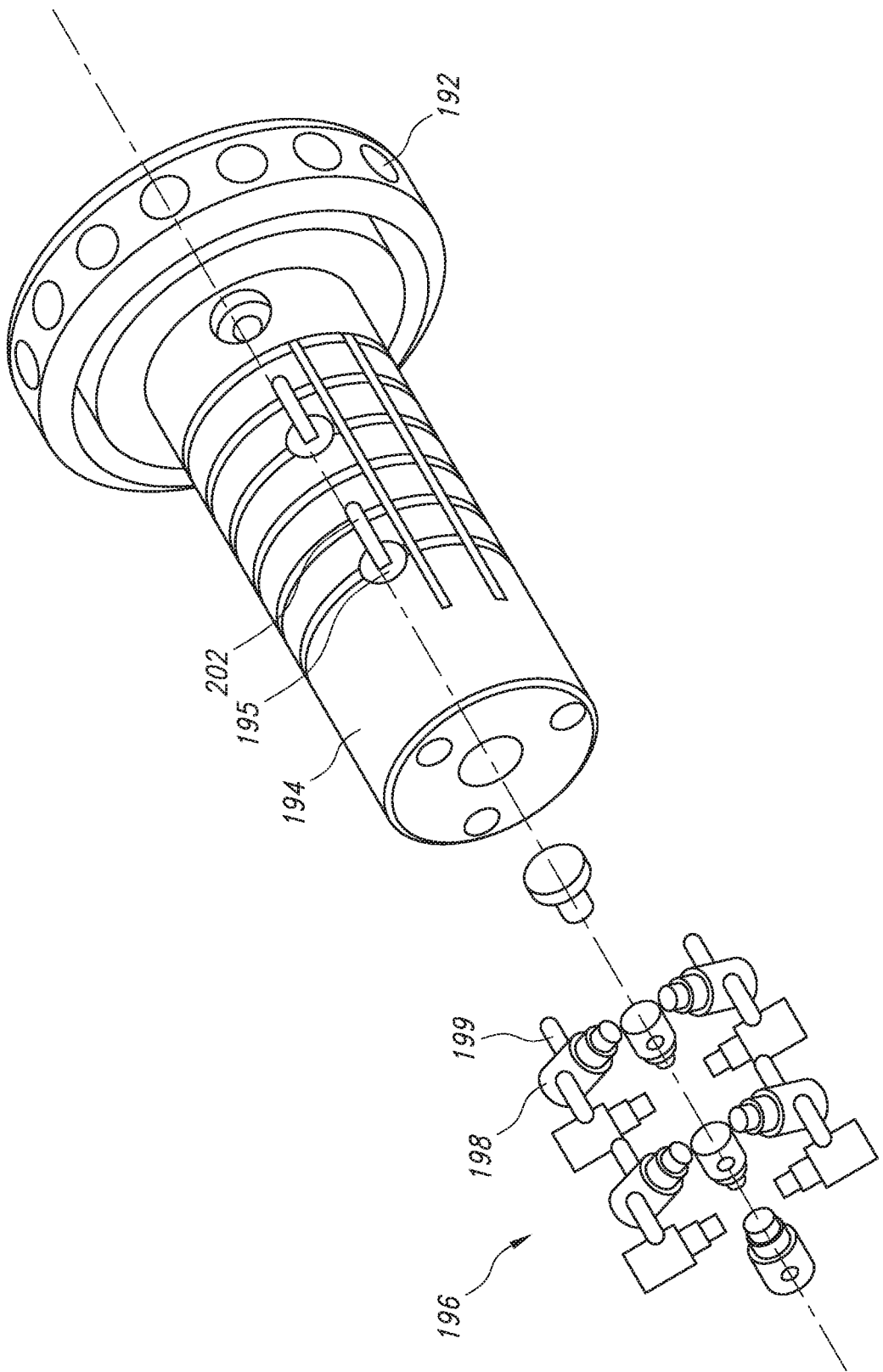
FIG. 5D is an isometric view of part of the receptacle of FIG. 5C.
Figure 5E:
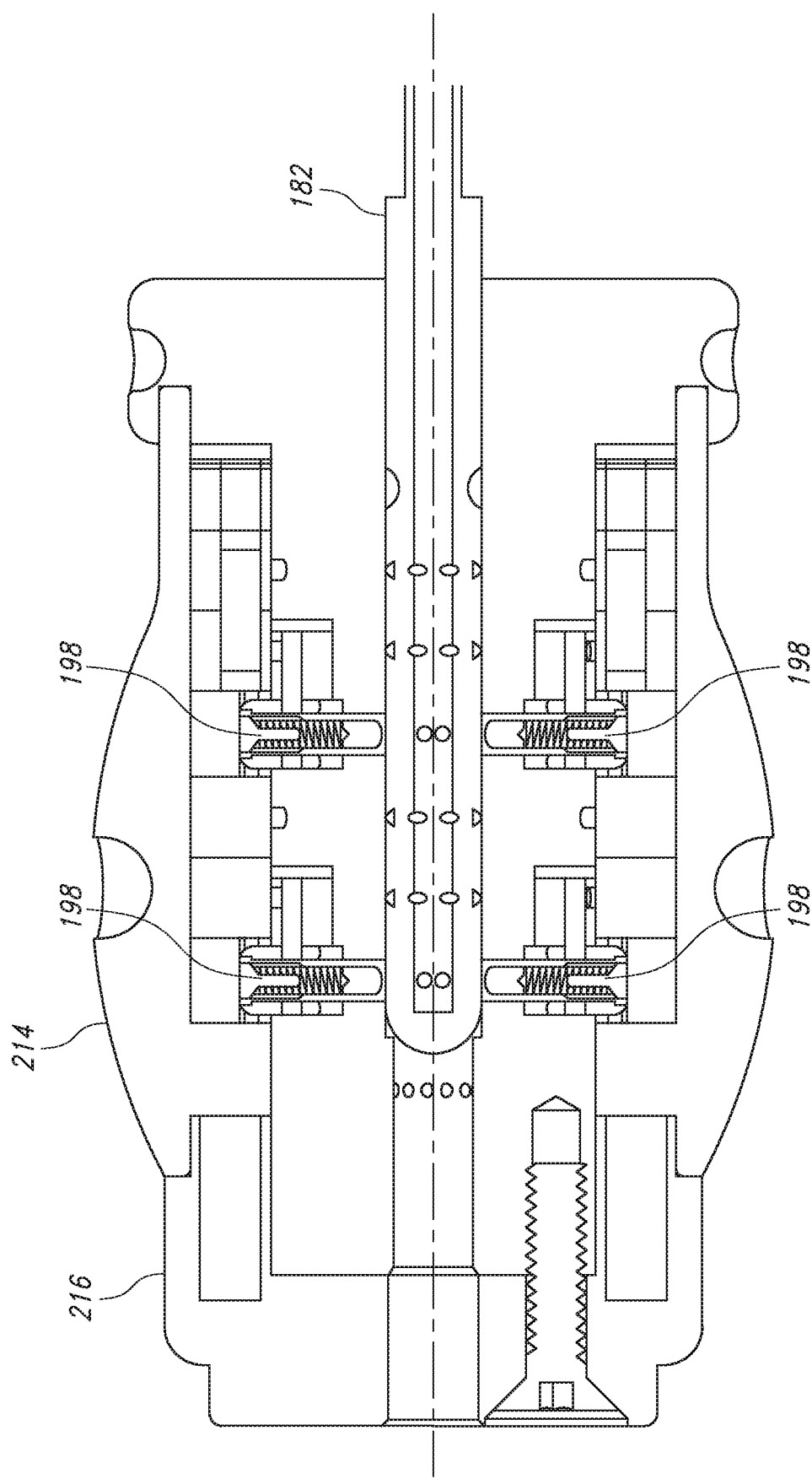
FIG. 5E is an exposed, side view of the connector assembly of FIG. 5A when in a connected position.

Referring to FIGS. 5C-D, the receptacle (190) includes a base (192) having a shaft portion (194) that extends through the length of the receptacle (190) when assembled. A pin assembly (196) containing a second plurality of pins (198) is disposed over the shaft portion (194). The pins (198) are connected to rods (199) that sit in channels (202) of the shaft portion (194). The shaft portion (194) has a plurality of apertures (195) through which the pins (198) will extend into the inner lumen of the shaft portion (194), as previously described.

A cam assembly with locking cam (212) are connected over the pin assembly (196). A knob (214) is mounted over the cam assembly, with a collar (216) securing it in place, with which the cam assembly is operated to descend or withdraw the pins (198) in the apertures (186) to lock or release the plug (182) in the receptacle (190).

The connector assembly (180) connects the proximal end of the elongated shaft (32) to the handle (40) by plugging the plug (182) into the receptacle (190). The pins (198) are spring loaded, such that when aligned with pins (188) of the plug (182), the pins (198) contact the pins (188), establishing an electrical connection therewith.

Figure 6:
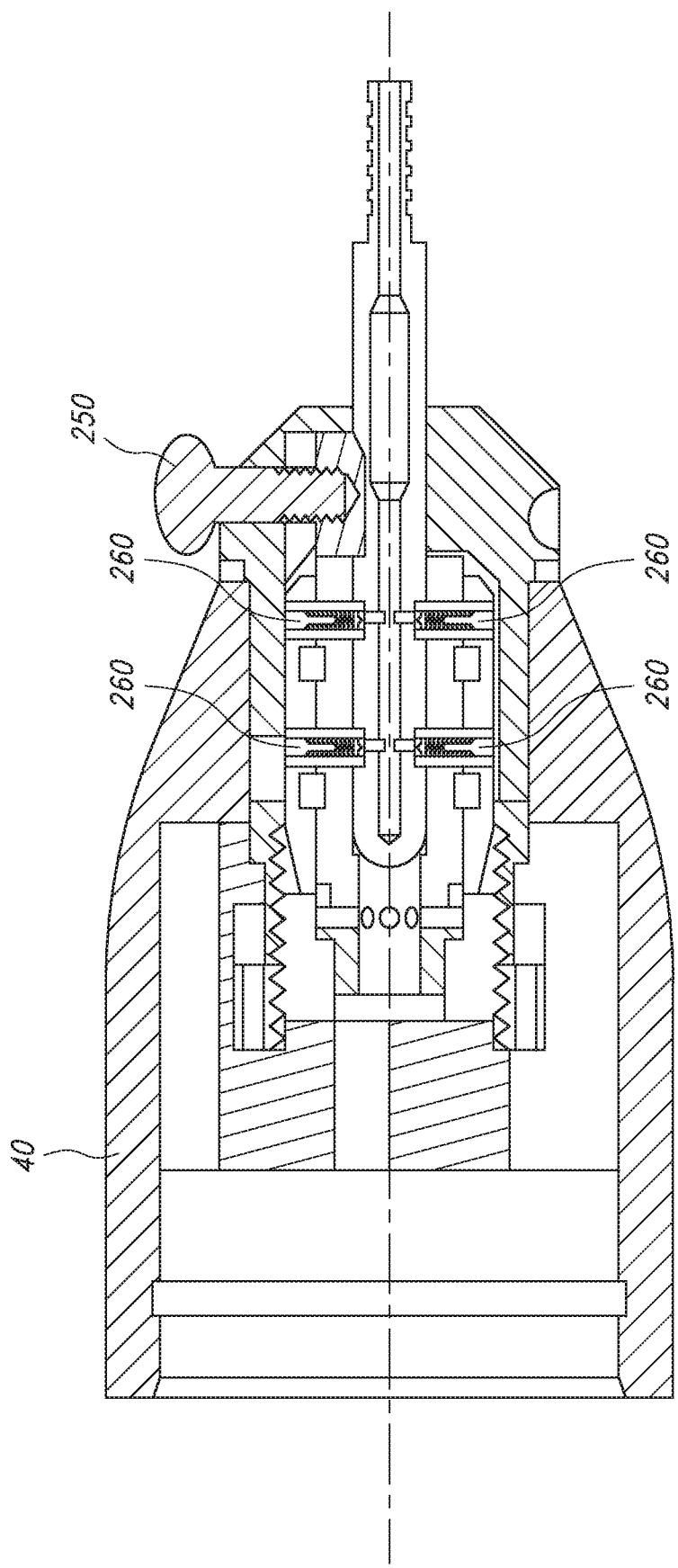
FIG. 6 is a cross-sectional view of the connector assembly of the imaging device of FIG. 2.

Referring to FIG. 6, in some embodiments, a button (250) is provided on the distal end of the handle (40), which can be pushed to actuate the cam mechanism that lifts the receptacle pins (260) to release the plug.

The catheter system of the present invention further includes a processor coupled to the imaging device for receiving and processing image data captured by the imaging device (30). Any suitable processor may be used in accordance with the present invention. For example, the processor may be included in the handle (40), or may be a separate device, such as a personal computer (45). In one advantageous embodiment, the processor is connected to the imaging device via a cable connection. In additional advantageous embodiments, the processor is connected to the imaging device via a wireless connection, which is desirable if a physician is located remotely from a patient being examiner or treated. Furthermore, the imaging device and/or the processor may be connected to an external storage device. The image data captured by the imaging device is stored on the storage device and may be later retrieved by a user. In other advantageous embodiments, the processor may have an internal storage device. Any suitable storage device may be used in accordance with the present invention.

The catheter system may further include a display coupled to the processor via a cable connection or via a wireless connection. The display receives imaging data processed by the processor and displays the image of the person's anatomy to a physician. Any suitable type of a display may be used in accordance with the present invention. In further advantageous embodiments, the catheter system further includes a user interface coupled to the processor. The user interface may be a graphical user interface (GUI), a keyboard, or any other suitable device that allows a user to input information and commands. The user interface is connected to the processor via a cable connection or via a wireless connection, and may be displayed on the display as on overlay image.

Figure 7A:
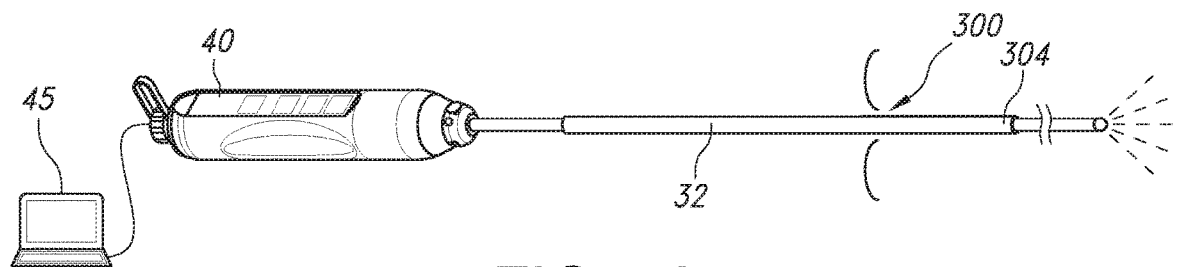
FIGS. 7A-E are schematic views of the operation of the imaging device of FIG. 2 in a bodily cavity.
Figure 7B:
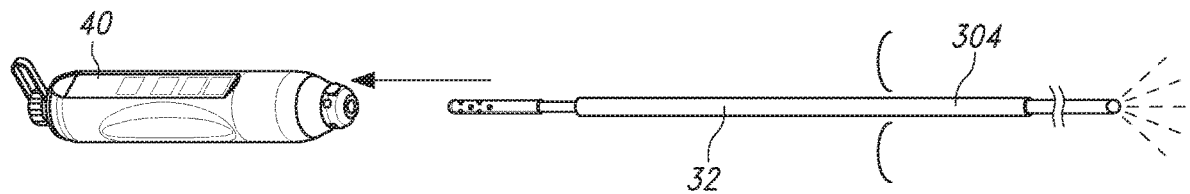
Figure 7C:
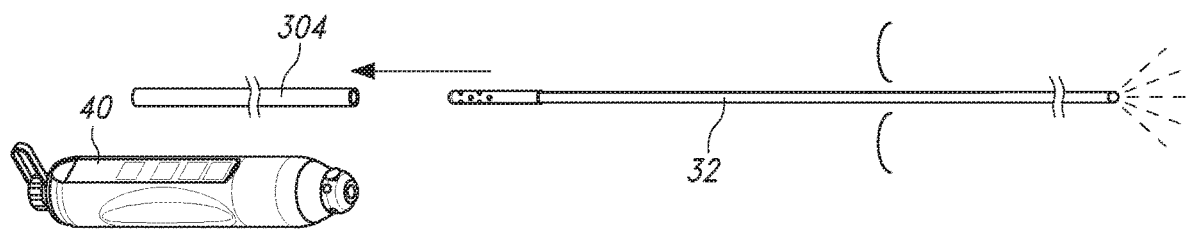
Figure 7D:
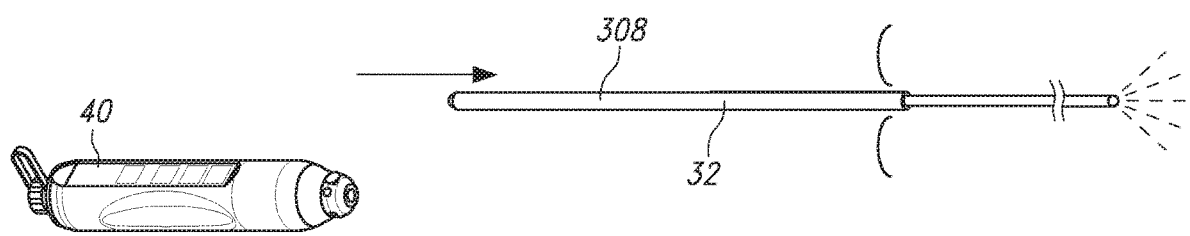
Figure 7E:
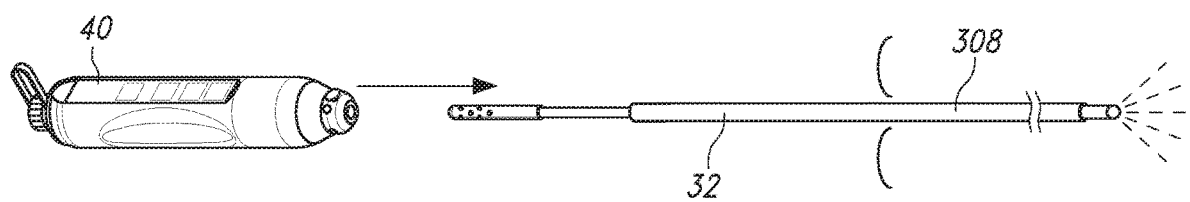

FIGS. 7A-E illustrate operation of the medical imaging device (30) of the present invention inside a bodily cavity (300). Referring first to FIG. 7A, the imaging device (30) is inserted into the bodily cavity via a surgical incision or a natural orifice through an outer cannula (304) and is then guided to the site of interest, where the image sensor obtains image data. When the user wishes to switch the outer cannula (304), the handle (40) is detached from the proximal end (36) of the shaft (32) via the connector assembly (80), as shown in FIG. 7B. The outer cannula (304) is then withdrawn from the bodily cavity over the elongated shaft (32), which remains in place, as illustrated in FIG. 7C. As shown in FIG. 7D, a new cannula (308) is advanced over the shaft (32) into the bodily cavity, using the shaft (32) as a guide. The handle (60) is then reattached to the proximal end (36) of the shaft (32) via the connector assembly (80).

It should be understood that the foregoing is illustrative and not limiting, and that obvious modifications may be made by those skilled in the art without departing from the spirit of the invention. Although the invention has been described with reference to embodiments herein, those embodiments do not limit the scope of the invention. Accordingly, reference should be made primarily to the accompanying claims, rather than the foregoing specification, to determine the scope of the invention.

What is claimed is:

1. A medical imaging device, comprising:
   an elongated shaft having a proximal end and a distal end;
   a handle detachably connected to the elongated shaft;
   a connector assembly by which the elongated shaft is detachably connected to the handle, the connector assembly comprising a plug at the proximal end of the elongated shaft, the plug having an outer wall, the plug including a first plurality of electrical terminals and a second plurality of electrical terminals, and the handle defining a receptacle having an inner wall defining a cavity that accommodates the plug;
   an image sensor at the distal end of the elongated shaft; and
   a plurality of electrical conductors electrically connected to the image sensor, extending through the elongated shaft, and electrically connected to the first plurality of electrical terminals in the plug,
   wherein the outer wall of the plug has a plurality of apertures through which the first plurality of electrical terminals establish an electrical connection with the second plurality of electrical terminals when the plug is inserted in the receptacle.

2. The medical imaging device of claim 1, wherein the plug has a longitudinal axis, and the second plurality of electrical terminals comprise a plurality of pins extending radially from the inner wall of the receptacle toward the longitudinal axis of the plug when the plug is inserted in the receptacle.

3. The medical imaging device of claim 1, wherein:
   the plug has a longitudinal axis,
   the first plurality of electrical terminals comprise a first plurality of pins extending radially from the longitudinal axis of the plug toward the outer wall; and
   the second plurality of electrical terminals comprise a second plurality of pins extending radially from the inner wall of the receptacle toward the longitudinal axis of the plug when the plug is inserted in the receptacle, such that the first plurality of pins contact the second plurality of pins when the plug is inserted in the receptacle.

4. The medical imaging device of claim 3, wherein the second plurality of pins are spring-loaded such that the first plurality of pins become aligned with the second plurality of pins as the plug in inserted into the receptacle.

5. The medical imaging device of claim 4, wherein the receptacle further comprises a cam that moves the second plurality of pins to release the plug.

6. The medical imaging device of claim 1, wherein at least some of the first plurality of electrical terminals are longitudinally or circumferentially offset from at least some others of the first plurality of electrical terminals.

7. The medical imaging device of claim 1, wherein the elongated shaft has an outer diameter of about 4 mm or less.

8. The medical imaging device of claim 1, wherein the image sensor comprises a CMOS sensor or a CCD sensor.

9. The medical imaging device of claim 1, further comprising at least one lens positioned distally of the image sensor.

10. The medical imaging device of claim 9, wherein the at least one lens comprises two plano-convex lenses positioned distally of the image sensor.

11. The medical imaging device of claim 1, further comprising at least one illumination device in the distal end of the elongated shaft.

12. The medical imaging device of claim 11, wherein the at least one illumination device comprises a plurality of LEDs arranged in the distal end of the elongated shaft.

13. A medical imaging device, comprising:
a elongated shaft having proximal end and a distal end;
a handle detachably connected to the elongated shaft;
a connector assembly by which the elongated shaft is detachably connected to the handle, the connector assembly comprising a plug at the proximal end of the elongated shaft, the plug having an outer wall, the plug including a first plurality of electrical terminals and a second plurality of electrical terminals, and the handle defining a receptacle that accommodates the plug;
an image sensor at the distal end of the elongated shaft; and
a plurality of electrical conductors electrically connected to the image sensor, extending through the elongated shaft, and electrically connected to the first plurality of electrical terminals in the plug,
wherein the outer wall of the plug has a diameter that is not greater than an outer diameter of the elongated shaft, and
wherein the first plurality of electrical terminals establish an electrical connection with the second plurality of electrical terminals when the plug is inserted in the receptacle.

14. The medical imaging device of claim 13, wherein the outer diameter of the elongated shaft is about 4 mm or less.

15. The medical imaging device of claim 13, wherein the image sensor comprises a CMOS sensor or a CCD sensor.

* * * * *